US008885793B2

(12) United States Patent
Dennerlein

(10) Patent No.: US 8,885,793 B2
(45) Date of Patent: Nov. 11, 2014

(54) SYSTEM AND METHOD FOR TOMOGRAPHIC RECONSTRUCTION IN THE 2D PARALLEL-BEAM GEOMETRY

(75) Inventor: Frank Dennerlein, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 220 days.

(21) Appl. No.: 13/540,588

(22) Filed: Jul. 2, 2012

(65) Prior Publication Data

US 2013/0003916 A1 Jan. 3, 2013

Related U.S. Application Data

(60) Provisional application No. 61/503,659, filed on Jul. 1, 2011.

(51) Int. Cl.
| | |
|---|---|
| *A61B 6/03* | (2006.01) |
| *A61B 6/00* | (2006.01) |
| *G06K 9/36* | (2006.01) |
| *G06T 11/00* | (2006.01) |

(52) U.S. Cl.
CPC .............. *A61B 6/03* (2013.01); *A61B 6/4085* (2013.01); *G06K 9/36* (2013.01); *A61B 6/4458* (2013.01); *A61B 6/504* (2013.01); *A61B 6/4233* (2013.01); *A61B 6/4441* (2013.01); *G06T 11/003* (2013.01)
USPC ............................................... 378/4; 382/131

(58) Field of Classification Search
CPC ...... A61B 6/03; G06T 11/003; G06T 11/005; G06T 11/006; G06T 2211/40
USPC ......................................... 378/4, 19; 382/131
See application file for complete search history.

(56) References Cited

U.S. PATENT DOCUMENTS

| | | | |
|---|---|---|---|
| 2005/0238219 A1* | 10/2005 | Roux et al. ..................... | 382/131 |
| 2009/0207964 A1* | 8/2009 | Pack ................................. | 378/4 |
| 2012/0014582 A1* | 1/2012 | Schaefer et al. .............. | 382/131 |
| 2013/0004045 A1* | 1/2013 | Dennerlein ................... | 382/131 |

\* cited by examiner

*Primary Examiner* — Glen Kao
(74) *Attorney, Agent, or Firm* — King & Spalding L.L.P.

(57) ABSTRACT

An alternative analytical method for tomographic reconstruction in the 2D parallel-beam geometry is presented. This method may follow a filtering and backprojection scheme and may involve a global filtering in the projection domain and a local filtering in the image domain. For example, the method may include applying Hilbert filtering to the received projection data, computing an antiderivative of the filtered data, backprojecting the antiderivative into the image domain, and computing the 2D Laplacian of the backprojection image.

2 Claims, 2 Drawing Sheets

SYSTEM AND METHOD FOR TOMOGRAPHIC RECONSTRUCTION IN THE 2D PARALLEL-BEAM GEOMETRY

CROSS-REFERENCE TO RELATED APPLICATIONS

This application claims priority to U.S. Provisional Patent Application No. 61/503,659 filed Jul. 1, 2011. The contents of which is incorporated herein by reference in its entirety.

TECHNICAL FIELD

This disclosure relates to image reconstruction, e.g., an analytical method for tomographic reconstruction in the 2D parallel-beam geometry, e.g., for user in an X-ray system.

BACKGROUND

Two-dimensional objects can be reconstructed from projections that were acquired using parallel projection rays. A practical algorithm for doing so is the Filtered Backprojection (FBP). It typically includes two steps: (1) filtering the projection data with a high-pass filter, and (2) backprojecting the filtered projections over the object domain. Three-dimensional objects, e.g., a can be reconstructed by assembling such 2D reconstructions, such that each 2D reconstruction forms a "slice" of the assembled 3D reconstruction. 3D reconstructions are used for various medical imaging. For example, 3D rotation angiography is a standard method used for estimating the vascular anatomy before and during interventions. Rotational angiography is a medical imaging technique based on x-ray, that allows to acquire CT-like 3D volumes during hybrid surgery or during a catheter intervention using a fixed C-Arm. The fixed C-Arm thereby rotates around the patient and acquires a series of x-ray images that are then reconstructed through software algorithms into a 3D image

SUMMARY

In one embodiment, a method for performing a tomographic reconstruction of an object in the 2D parallel-beam geometry may include receiving projection data associated with an object; applying Hilbert filtering to the received projection data; computing an antiderivative of the filtered data; backprojecting the antiderivative into the image domain; and computing the 2D Laplacian of the backprojection image.

In another embodiment, a system for performing a tomographic reconstruction of an object in the 2D parallel-beam geometry may include an X-ray source; an X-ray detector configured to detect radiation from the X-ray source to collect projection data associated with an object; and a processing circuit configured to perform a tomographic reconstruction of the object by applying Hilbert filtering to the collected projection data, computing an antiderivative of the filtered data, backprojecting the antiderivative into the image domain, and computing the 2D Laplacian of the backprojection image.

BRIEF DESCRIPTION OF THE DRAWINGS

Example embodiments will be explained in more detail below with reference to figures, in which.

DETAILED DESCRIPTION

The reconstruction approach of the present disclosure is discussed below.

Figure 1:
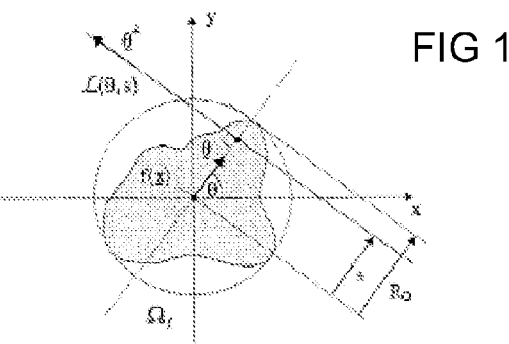
FIG. 1 is an illustration of the 2D parallel-beam geometry for describing a tomographic reconstruction.

FIG. 1 illustrates a standard notation used in this disclosure to describe the 2D parallel-beam acquisition geometry and the quantities occurring during reconstruction. The investigated object is described with $f(\underline{x})$. One black, example line $\pounds(\theta,s)$ is shown, which is orthogonal to $\underline{\theta}$, parallel to $\underline{\theta}^\perp$. and has distance $|s|$ from the origin of the 2D image plane.

In the following description, 2D parallel-beam data will be denoted with a function g that can be defined as $$g(\theta,s)=\int_{-\infty}^{\infty} f(s\underline{\theta}+t\underline{\theta}^\perp)dt. \quad (1)$$

We assume that this function is known for $\theta \in [0, \pi)$ and for all values of s at which g is non-zero. For convenience, the short-hand notations $g_F$ and $g_H$ will be introduced that denote the filtered parallel-beam projections convolved with the ramp filter $h_r$ or the Hilbert filter $h_h$, respectively. The formal definitions of these filtered projections are $$gF(\theta,s)=\int_{-\infty}^{\infty} h_r(s-s')g(\theta,s')ds'$$

and $$gH(\theta,s)=\int_{-\infty}^{\infty} h_h(s-s')g(\theta,s')ds'. \quad (2)$$

The classical, ramp-filter based parallel-beam FBP reconstruction formula (e.g., as described in "*Principles of Computerized Tomographic Imaging, Chapter* 3.3 *Reconstruction Algorithms for Parallel Projections,*" A. C. Kak and M. Slaney, IEEE Press, 1988) can be expressed as $$f(\underline{x})=\int_0^\pi gF(\theta,\underline{x}\cdot\underline{\theta})d\theta \quad (3)$$

and reformulated into the equivalent expression $$f(\underline{x}) = \int_0^\pi \frac{\partial^2}{\partial s^2} g_1(\theta, s)\bigg|_{s=\underline{x}\cdot\underline{\theta}} d\theta \quad (4)$$

where $$g_1(\theta, s) = \frac{1}{2\pi}\int_{-\infty}^s g_H(\theta, s')ds'.$$

In this equation, the function $g_1$ is the antiderivative of the Hilbert-filtered, scaled projection data at fixed angle $\theta$. Hence, the function $g_F$ can be obtained by differentiating $g_1$ twice with respect to s, and this fact is used in the reformulation presented above. In the next part of the derivation, we follow a scheme similar to that described in "*A new class of upper-short-scan algorithms for fan-beam reconstruction*". (I. Arai, H. Kudo, F. Noo, M. Defrise, and J. D. Pack, published in *IEEE Nuclear Science Symposium Conference Record*, volume 4, pages 2296-2300, Puerto Rico, USA, 2005) to obtain:

$$\left.\frac{\partial^2}{\partial x^2}g_1(\theta, s)\right|_{s=\underline{x}\cdot\underline{\theta}} = \left.\frac{\partial^2}{\partial s^2}g_1(\theta, s)\right|_{s=\underline{x}\cdot\underline{\theta}} \cos^2\theta \qquad (5)$$

and $$\left.\frac{\partial^2}{\partial y^2}g_1(\theta, s)\right|_{s=\underline{x}\cdot\underline{\theta}} = \left.\frac{\partial^2}{\partial s^2}g_1(\theta, s)\right|_{s=\underline{x}\cdot\underline{\theta}} \sin^2\theta. \qquad (6)$$

Using the properties of trigonometric functions, these both findings can be combined into $$\left(\frac{\partial^2}{\partial x^2} + \frac{\partial^2}{\partial y^2}\right)g_1(\theta, \underline{x}\cdot\underline{\theta}) = \left.\frac{\partial^2}{\partial s^2}g_1(\theta, s)\right|_{s=\underline{x}\cdot\underline{\theta}} \qquad (7)$$

and substituted into the left-hand-side of (4) to obtain $$f(\underline{x}) = \left(\frac{\partial^2}{\partial x^2} + \frac{\partial^2}{\partial y^2}\right)\int_0^\pi \frac{1}{2\pi}\int_{-\infty}^{\underline{x}\cdot\underline{\theta}} g_H(\theta, s')ds'd\theta. \qquad (8)$$

Figure 2:
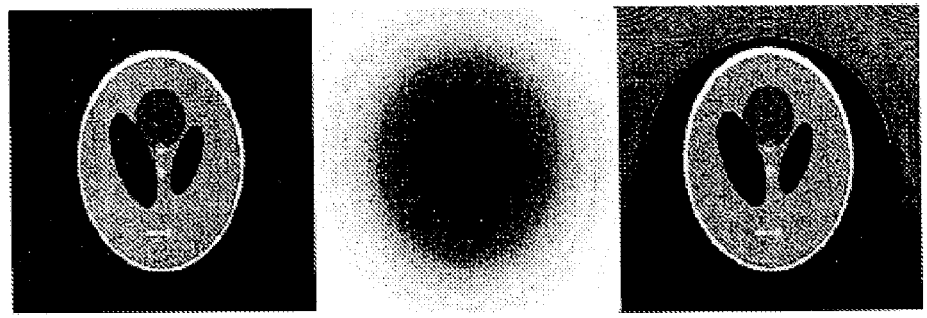
FIG. 2 illustrates an example reconstruction of the Shepp-Logan phantom, according to a known ramp-filter based FBP process (left), a backprojection result during the method disclosed herein (center), and the final resulting reconstruction after applying the 2D Laplace operator according to the method disclosed herein (right).

FIG. 2 illustrates an example reconstruction of the Shepp-Logan phantom, according to a classical, ramp-filter based FBP (left), a backprojection result after the backprojecting the antiderivative into the image domain, according to the method disclosed above (center), and the final resulting reconstruction after applying the 2D Laplace operator, according to the method disclosed above (right). The final reconstructions are shown in the grayscale window.

Thus, in embodiments of the method disclosed herein, an image reconstruction may be obtained by the following method:
  Step 1: Hilbert filtering of projection data
  Step 2: Computing the antiderivative of the filtered data
  Step 3: Backprojecting the antiderivative into image domain
  Step 4: Computing the 2D Laplacian of the backprojection image For diagnostic examination purposes and for interventional procedures in for example cardiology, radiology and neurosurgery, interventional X-ray systems are used for imaging, the typical essential features of which systems can be a C-arm on which an X-ray tube and an X-ray detector are mounted, a patient positioning table, a high-voltage generator for generating the tube voltage, a system control unit, and an imaging system including at least one monitor.

Figure 3:
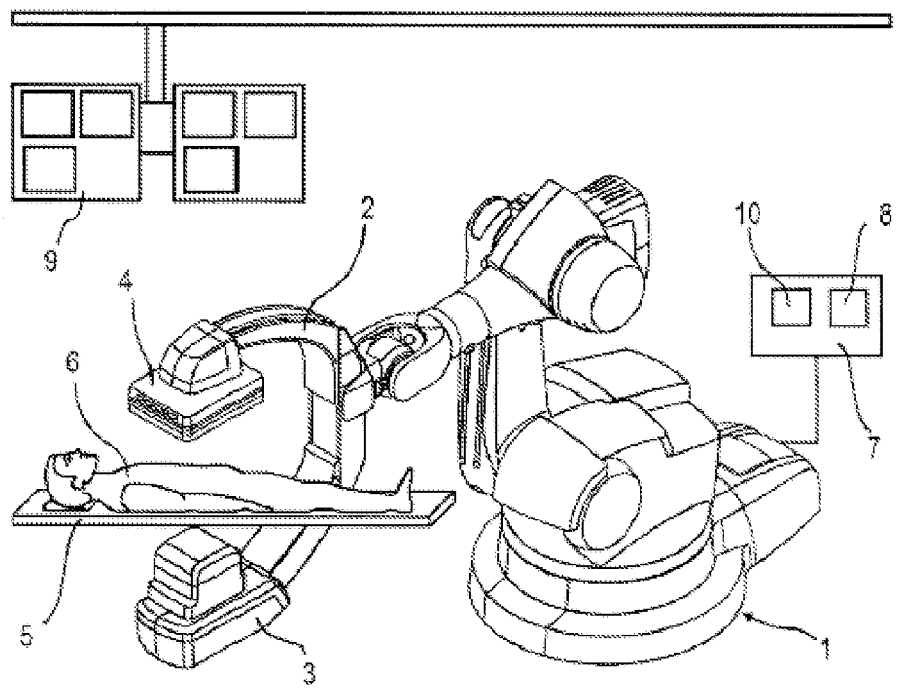
FIG. 3 illustrates an example C-arm X-ray imaging system configured or programmed to implement the method disclosed herein, according to one embodiment.

FIG. 3 illustrates an example C-arm interventional X-ray imaging system configured or programmed to implement the method disclosed herein, according to one embodiment. The example system may include a C-arm 2 which is rotatably mounted on a stand in the form of a six-axis industrial or articulated-arm robot 1 and at the ends of which are mounted an X-ray radiation source, for example an X-ray tube assembly 3 with X-ray tube and collimator, and an X-ray image detector 4 as image acquisition unit.

The articulated-arm robot 1, which may have six axes of rotation and hence six degrees of freedom, may enable the C-arm 2 to be moved to an arbitrary position in space, for example by being rotated around a center of rotation between the X-ray tube assembly 3 and the X-ray detector 4. The X-ray system can be rotated in particular around centers of rotation and axes of rotation in the C-arm plane of the X-ray image detector 4, e.g., around the center point of the X-ray image detector 4 and around axes of rotation intersecting the center point of the X-ray image detector 4.

The known articulated-arm robot 1 may include a base frame permanently installed on a floor, for example. A carousel may be attached to the robot, which carousel may be rotatable about a first axis of rotation. A robot rocker may be mounted on the carousel so as to be pivotable about a second axis of rotation. A robot arm that is rotatable about a third axis of rotation may be attached to the rocker. A robot hand that is rotatable about a fourth axis of rotation may be mounted at the end of the robot arm. The robot hand may include a retaining element for the C-arm 2, the retaining element being pivotable about a fifth axis of rotation and rotatable about a sixth axis of rotation running perpendicular thereto.

The X-ray image detector 4 can be a rectangular or square, flat semiconductor detector which may be produced from amorphous silicon (a-Si), for example. Integrating or counting CMOS detectors can also be used, however.

A patient 6 to be examined is placed as the examination subject in the beam path of the X-ray tube assembly 3 on a patient positioning table 5 so that images of the heart, for example, can be recorded. Connected to the X-ray diagnostic apparatus is a system control unit 7 having an imaging system 8 and a processing circuit 10 that process the image signals from the X-ray image detector 4 (control elements are not shown, for example). X-ray detector 4 may collect projection data, and pass such data (directly or indirectly, e.g., for intermediate processing) to processing circuit 10. The processing circuit 10 may be configured to perform a tomographic reconstruction to generate X-ray images as discussed above, e.g., by a process including applying Hilbert filtering to the collected projection data, computing an antiderivative of the filtered data, backprojecting the antiderivative into the image domain, and computing the 2D Laplacian of the backprojection image, as discussed above. The X-ray images can then be viewed on a monitor 9.

Figure 4:
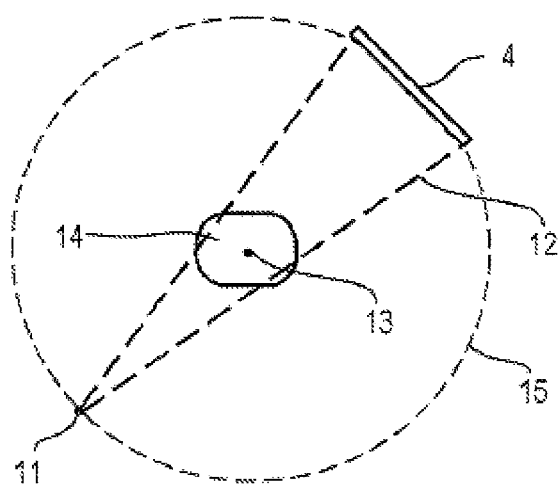
FIG. 4 illustrates an X-ray source and detector of the example system of FIG. 3, being configured to rotate around the subject, according to one embodiment.

The X-ray tube assembly 3 emits a bundle of rays 12 originating from a beam focus 11 of its X-ray radiation source and striking the X-ray image detector 4. If it is intended to generate 3D data sets according to the so-called DynaCT method for low-contrast visualization of for example soft tissue, the rotatably mounted C-arm 2 with X-ray tube assembly 3 and X-ray image detector 4 may be rotated in such a way that, as FIG. 4 shows schematically in a view onto the axis 13 of rotation, the X-ray tube assembly 3—represented figuratively here by its beam focus 11 as well as the X-ray image detector 4—moves around an examination subject 14 located in the beam path of the X-ray tube assembly 3 on an orbit 15. The orbit 15 can be traversed completely or partly for the purpose of generating a 3D data set.

In this case the C-arm 2 with X-ray tube assembly 3 and X-ray image detector 4 may move according to the DynaCT method, e.g., through an angular range of at least 180°, for example 180° plus fan angle, and record projection images in rapid succession from different projections. The reconstruction can be carried out based on just a subset of said acquired data, e.g., using the method discussed above. The subject 14 to be examined can be for example an animal or human body or indeed a phantom body.

The X-ray tube assembly 3 and the X-ray image detector 4 each rotate about the object 5 in such a way that the X-ray tube assembly 3 and the X-ray image detector 4 are disposed on opposite sides of the subject 14.

In normal radiography or fluoroscopy by means of an X-ray diagnostic apparatus of this type the medical 2D data of the X-ray image detector 4 may be buffered in the imaging system 8 if necessary and subsequently displayed on the monitor 9.

What is claimed is:

1. A method for performing a tomographic reconstruction of an object in 2D parallel-beam geometry, comprising:
    receiving, by a processing circuit from an X-ray detector, projection data associated with an object;
    applying, by the processing circuit, Hilbert filtering to the received projection data;
    computing, by the processing circuit, an antiderivative of the filtered data;
    backprojecting, by the processing circuit, the antiderivative into the image domain; and
    computing, by the processing circuit, the 2D Laplacian of the backprojection image.

2. A system for performing a tomographic reconstruction of an object in 2D parallel-beam geometry, comprising:
    an X-ray source;
    an X-ray detector configured to detect radiation from the X-ray source to collect projection data associated with an object; and
    a processing circuit configured to perform a tomographic reconstruction of the object by:
        applying Hilbert filtering to the collected projection data;
        computing an antiderivative of the filtered data;
        backprojecting the antiderivative into the image domain; and
        computing the 2D Laplacian of the backprojection image.

* * * * *